United States Patent [19]

Strommen

[11] Patent Number: 4,703,254
[45] Date of Patent: Oct. 27, 1987

[54] PROBE FOR CORROSION TESTING

[76] Inventor: Roe Strommen, Rydningen 23B, N-7000, Trondheim, Norway

[21] Appl. No.: 772,378

[22] Filed: Sep. 4, 1985

[30] Foreign Application Priority Data

Mar. 6, 1985 [NO] Norway .................................. 840831

[51] Int. Cl.⁴ ...................... H01C 17/00; H01C 13/00
[52] U.S. Cl. ............................. 324/65 CR; 204/129.2; 338/195
[58] Field of Search ............... 324/65 D, 65 CR, 71.2; 338/195; 204/1 T, 129.2

[56] References Cited

U.S. PATENT DOCUMENTS 2,987,672 6/1961 Marsh ........................... 324/65 CR
3,104,355 9/1963 Holmes ......................... 324/65 CR

FOREIGN PATENT DOCUMENTS 1402413 6/1975 United Kingdom .

Primary Examiner—Reinhard J. Eisenzopf
Assistant Examiner—Jose M. Solis
Attorney, Agent, or Firm—James E. Pittenger

[57] ABSTRACT

Probe for testing of corrosion, to having a helically arranged resistance element on a rodshaped carrier of electrically insulating material. The carrier is embedding a reinforcing core being used as a conductor to the free end of the resistance element. The resistance element has an exposed half and a half covered by a nonconductor, providing an active part and a reference part to be connected in a bridge circuit for temperature compensated measurements.

5 Claims, 2 Drawing Figures

PROBE FOR CORROSION TESTING

This invention relates to a probe as described in the introductory part of claim 1, for testing of corrosion. The probe is particularly designed to be permanently installed, e.g. in the wall of a pipe or a tank, and to be connected to a remote measurement circuit.

Probes for testing corrosion are used in various systems, e.g. in systems for processing petrochemical products, particularly offshore. Such probes are preferably made from an active, metallic material of a material similar to that of the equipment to be protected and are fitted with threads to be screw mounted to bring this active, exposed part of the probe in contact with the same medium as the equipment itself, e.g. the medium transported in a pipe. The active part of the probe is electrically connected to a remote measurement circuit.

One principle for such measurement is based on measurement of the electrical resistance in the exposed, metallic part of a probe and the comparison with the resistance of a similar, unexposed part. By decreasing area of the corroded element, the electrical resistance will increase and present a measure of the corrosion of the equipment concerned. Such probes are generally termed "electrical resistance probes" or ER-probes. Such ER-probes may have an additional part of the same properties, but sealed from the influence of the corrosive environment and acting as a reference element. This will enable a desirable temperature compensation.

The British Pat. No. 1.402.413 discloses a probe developed for such measurements, wherein a helical conductive element is arranged on an electrically nonconductive, rod shaped core. Besides from the mechanical inferiority of the core material, this design will suffer from the disadvantage of having a separate electrical conductor attached to each end of the resistance element, complicating the mounting. Further, the conductive element is liable to be attacked by particular corrosion in the fissures created between the core and the conductive element, which will render a false measurement.

The main object of the invention thus is to create a novel and improved probe of the kind described, with mechanical and measurement properties superior to the known probes. Particularly it is an object to create a probe which is easy to mount in the wall pipe or of a tank and which is designed for comparative measurements, allowing temperature compensation.

According to the invention, this can be achieved by providing a probe as described in claim 1.

Further advantageous features of the invention are described in the subclaims.

The invention will now be described further with the reference to the drawings, in which.

Figure 1:
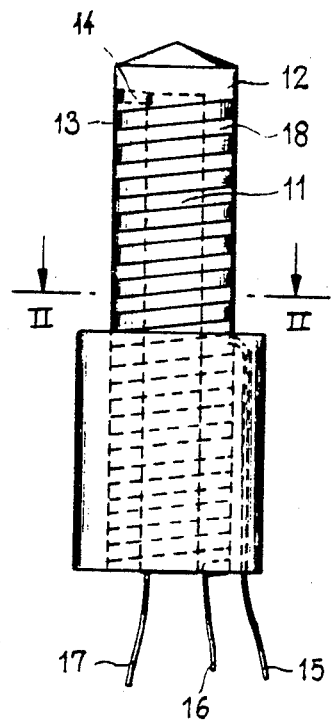
FIG. 1 shows a side view of an embodiment of the invention.
Figure 2:
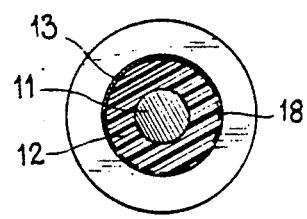
FIG. 2 shows a section along the line II—II in FIG. 1.

The embodiment of FIGS. 1 and 2 comprises a cylindrical rod 11 of steel or other electrically conducting material with corresponding physical properties. The main part of this rod 11 and its one end is covered by a sheathing 12 of a synthetic, preferably elastomer, electrically insulating material.

The insulating sheathing 12, which can have the character of a hollow cylinder with the rod firmly embedded inside, is carrying a helically wound strip 13 of a carbon steel or other metallic material, depending on the material of the structure where the corrosion is to be tested. The strip 13, which is wound or otherwise arranged on the surface of the sheathing 12, has a pitch which is larger than its width, leaving a helical insulating passage along the strip.

The end of the strip 13 adjoining the closed end of the sheathing is electrically connected to the central rod 11 as indicated at 14. The center of the strip 13 is connected to an electrically insulated wire 15, while the other end of the strip 13, adjoining the free end of the rod 11, is connected to an electrically insulated wire 16. To the free end of the rod 11, an electrically conductive wire 17 is connected.

The passage between the coils of the strip 13 is covered by an electrically insulating material 18, leaving the surface of the structure with the free surface of the strip and the adjoining surface plain.

The inner part of the strip 13 is covered by a housing 19, making the surface of this half of the strip 13 unaccessible. The housing 19 is preferably moulded to make a sealed bond to the carrying structure. In a modified embodiment, the strip 13 is provided with its carrying and covering parts by a moulding process. The necessary electrical connections then have to be prepared prior to the moulding process.

The housing 19 is provided partly to cover one half of the strip 13, and partly to mount the probe in the wall of a structure in which the corrosion is to be tested, e.g. a pipe or a tank. For this purpose it can be provided with threads (not shown) or otherwise made suitable for mounting in an opening, such as a bore or a bushing.

The wires 15, 16, and 17 are connected to a measuring circuit (not shown) to place the two parts of the strip 13 as the two limbs of a measuring bridge. Thus the exposed, outer part of the strip 13 will have a comparable reference part embedded within the housing.

The rod 11, besides functioning as an electrical conductor, has an important function as reinforcement of the probe.

The diameter of the free part of the probe shown may be 10–30 mm and the length of the protruding, free part 10–100 mm. Suitable physical properties of the materials to be used may well be determined by a person skilled in the art. The strip 13 is preferably prepared of a material with resistance to corrosion corresponding to that of the structure to be tested.

The length of the strip 13 may be 400 mm, its width 3 mm and its thickness 1 mm.

The probe may be modified, as to the method of manufacturing, dimensions, shape of section and the selection of the materials. Such modifications are considered to be within the scope of the invention as defined in the accompanying claims.

I claim:

1. A probe for corrosion testing having a helically wound resistance element fabricated from a test material, said helically wound resistance element being formed around an electrically insulating core, the probe improvement consisting of an elongated electrically conducting reinforcement member arranged within said insulating core, a first end of said resistance element nearest a first end of said reinforcement member is electrically connected to said reinforcement member, a portion of the helical resistance element wound on said electrically insulating core is sealingly covered by a housing member whereby the corrosive atmosphere cannot reach and attack the covered portion of said resistance element to provide a temperature compensating reference portion, the remaining portion of said helical resistance element being left exposed, and electrical conductors are connected intermediate to the resistance element at the edge of said housing member and at the opposite end of the resistance element and the reinforcement member from their first ends so that the conductors can be connected to a measurement circuit whereby the resistance change of the exposed element portion with respect to the covered element portion will indicate the results of the corrosion test.

2. Probe according to claim 1, characterized in that the length of the covered part and the exposed portion of the resistance element are equal.

3. Probe according to claim 1, characterized in that it comprises an electrically insulating member arranged between the helices of the helically wound resistance element, to seal the surface of the exposed portion of the probe and make it flush.

4. Probe according to claim 1, characterized in that the core and the housing are moulded of a synthetic elastomer material as an integrated part.

5. Probe according to claim 1, characterized in that the probe is arranged for mounting in the wall of a vessel or pipe where the corrosion is to be tested, to have the portion of the probe with the exposed resistance element protruding into said vessel or pipe.

* * * * *